(12) United States Patent
Smith

(10) Patent No.: US 7,985,425 B1
(45) Date of Patent: Jul. 26, 2011

(54) NON-PHARMACOLOGICAL METHOD FOR TREATING DEPRESSION, SKIN DISORDERS AND IMPROVING OVERALL HEALTH AND WELLNESS

(76) Inventor: Jack V. Smith, Arden, NC (US)

( * ) Notice: Subject to any disclaimer, the term of this patent is extended or adjusted under 35 U.S.C. 154(b) by 0 days.

(21) Appl. No.: 10/250,223

(22) Filed: Jun. 13, 2003

Related U.S. Application Data

(63) Continuation-in-part of application No. 10/004,981, filed on Dec. 7, 2001, now abandoned.

(51) Int. Cl.
*A61K 51/00* (2006.01)
*A61K 9/14* (2006.01)
(52) U.S. Cl. ........................ 424/488; 424/1.73
(58) Field of Classification Search .............. 435/173.1, 435/1; 422/1; 424/400
See application file for complete search history.

(56) References Cited

U.S. PATENT DOCUMENTS

| | | | | |
|---|---|---|---|---|
| 190,374 | A | * | 5/1877 | Howard ........................ 70/263 |
| 5,417,994 | A | * | 5/1995 | Chang et al. ............... 426/330.3 |
| 5,688,532 | A | * | 11/1997 | Bryce-Smith ................ 424/641 |
| 6,063,406 | A | * | 5/2000 | Hornack ...................... 424/678 |
| 6,165,964 | A | * | 12/2000 | Nishimoto et al. ........... 510/383 |
| 6,496,727 | B1 | * | 12/2002 | Bernhard et al. ............. 604/20 |
| 6,555,543 | B2 | * | 4/2003 | Bar-Or et al. ............ 514/255.02 |
| 2005/0100804 | A1 | * | 5/2005 | Tamoto et al. .................. 430/66 |

OTHER PUBLICATIONS

Toyota Central R&D Labs., Inc., "Influence of Negative Air Ions on Drivers" 2002, only one page.*
Chopin et al, new Phytol. "Polyphosphates in the red macroalga *Chondrus crispus*." 135(4): pp. 587-594, 1997.*

* cited by examiner

*Primary Examiner* — Debbie K Ware
(74) *Attorney, Agent, or Firm* — Anton J. Hopen; Smith & Hopen, P.A.

(57) ABSTRACT

The present invention is a method for manufacture and treatment of depression and health disorders using a non-pharmacologic stable negative ion solution.

11 Claims, No Drawings

NON-PHARMACOLOGICAL METHOD FOR TREATING DEPRESSION, SKIN DISORDERS AND IMPROVING OVERALL HEALTH AND WELLNESS

CROSS REFERENCE TO RELATED APPLICATIONS

This is a continuation-in-part of U.S. patent application Ser. No. 10/004,981 filed Dec. 7, 2001 the specification of which is incorporated herein by reference.

BACKGROUND OF THE INVENTION

1. Field of the Invention

The present invention is a method that relates to a liquid-stable solution of negative ions (to be referred to as "ions") that has been proven in research with the ability to provide a non-pharmacologic therapy for the following health issues. Negative ions have been proven to have a positive affect on behavioral disorders (i.e. seasonal affective disorder (SAD)), relief of depression, relief from headaches, earaches, stuffy/snotty noses from hay-fever allergies or colds, for the treatment of asthma, bronchitis, thromboembolism, pain and peeling from sunburn or other burns, itch relief from psoriasis, bug bites, or other skin irritations, as well as, improving memory, vitamin metabolism, sleeping patterns and behavior. The ions solution can be applied directly, sprayed, or misted on skin, and can also be inhaled. The ions solution can be placed in spray bottles, misters, humidifiers, or other devices to disperse the solution into the air. Additionally, the ions solution can be used as a drink for internal intake.

It is therefore an object of the present invention to provide a non-pharmacologic method for treating health and behavioral issues such as SAD, depression, headaches, earaches, stuffy/snotty noses from hay-fever allergies or colds, asthma, bronchitis, thromboembolism, pain and peeling from sunburn or other burns, itching from psoriasis, bug bites, or other skin irritations, as well as, a method for improving memory, vitamin metabolism, sleeping patterns and behavior. The aforementioned results may be attained by exposing a patient to high density negative ions by directly using a liquid-stable solution of negative ions via bathing, spray or mist aerosols, humidifier, mister, inhaler, drinking or other mode of application to the skin or internal intake.

A further objective is to provide a method for the treatment of patients, determined to have certain health and behavioral issues, by exposure to high concentration of negative ions in a liquid-stable matrix for a predetermined course of time.

2. Description of the Related Art

The present invention is a method that relates to a liquid stable solution of negative ions (to be referred to as "ions"). Negative ions have been demonstrated in numerous research papers and publications as having the ability to provide a non-pharmacologic therapy solution for many health and behavior issues. The present art can be applied directly, sprayed, or misted on skin, and can also be inhaled. The ions solution can be placed in spray bottles, misters, humidifiers or other devices to disperse the solution into the air, and can also be used as a drink for internal intake.

There is no prior art that demonstrates, teaches or even alludes to a liquid-stable solution of negative ions that can be used a for non-pharmacologic treatment for depression, behavioral disorders (i.e. seasonal affective disorder (SAD)), headaches, earaches, stuffy noses from hay-fever allergies or colds, asthma, bronchial asthma, and bronchitis, thromboembolism, pain and peeling from sunburn or other burns, itching from psoriasis, bug bites, or other skin irritations, as well as, improving memory, vitamin metabolism, sleeping patterns and behavior.

About 13 million Americans suffer from winter depression at a fully syndromal level, and approximately another 30 million suffer a milder form of subsyndromal level that may not meet diagnostic severity criteria. There is prima facie evidence that reduced daylight availability in fall and winter is a likely precipitant of the depressive episode. It has been demonstrated, although not understood, that bright light, as well as, negative ions can be an effective treatment for depression. It has been demonstrated that, in addition to possibly having a profound effect on mood and energy, negative ions may have a strong impact on cognitive functioning. In 1965, the journal, "Psychophysiology", a study, "Behavioral Effects of Ionized Air on Rats", was published. In the study, the mental functioning of rats was tested for the effects of negative ions On page 358 of the journal, researchers reported that: "the water-maze performance improved 350%," showing a dramatic improvement in cognitive functioning. Another article on negative ions published in April of 1978, in the science journal of "Ergonomics", a study performed at the University of Surrey, England, entitled, "Air Ions and Human Performance". Additionally, demonstrated that negative ions have a positive effect on cognitive functions. A quote from the article reads: "Three testing environments were used: natural, negative, and positive ionizations. Negative ionization was associated with a significant increment in performance as compared to controls.

Dr. Albert Kreuger, professor emeritus of the University of California at Berkeley, performed research on negative ions in the 1950's. Dr. Kreuger excited the scientific world when he discovered ions to be biologically active, stimulated production of the powerful chemical serotonin (5-hydroxytryptamine), which is present in many tissues (especially blood) and is a very active neuro-hormone causing profound neural, glandular, and digestive effects that includes stimulation of smooth muscles and nerves. It has been well published that serotonin may be important in controlling sleep.

In a 1995 issue of "Journal of Alternative and Comparative medicine" a double-blind study was performed by Dr. Michael Terman (head of Columbia's Winter Depressions Department) and Dr. Jivan Si Terman on the impact of negative ion therapy on people suffering from seasonal affective disorder (winter depression). The study produced remarkable results, including, "While a low negative ion generator provided little benefit, a high density negative ion generator gave relief from depression compatible to that given by Prozac and other antidepressants, without drug side effects." Dr. Bob Arnot performed a study published in the "Journal of Alternative and Complementary Medicine" and concluded that patients exposed to high-density negative ions had significant relief of their symptoms for depression almost identical to drugs, but without drug side effects. A patient under Dr. Arnot's care stated, "While I was on treatment, I felt excited, I felt energized. I felt alive.

A scientific article from the research papers of Bionic Products PTY., LTD. titled, "The Treatment of Bronchial Asthma by Negative Aeroionization" stated in the conclusion that "treatment with negative aerions (therapeutic dose of 100 150 million aerions per session) leads to an improvement in the general state of the patients, a normalization of the blood picture, of the vascular and respiratory reactions, etc. Results of treatment: a) dyspnoeic attacks disappear in 55% of patients within 6 months; b) the intensity and number of attacks is reduced in 35% of patients; c) treatment is ineffective in 10% of cases. Negative aerions normalize the functional state of the central nervous system and in all cases the system of the patients with asthma."Another published study titled, "Prevention of Post-Operative Thromboembolism by Negative Air Ionization in a Double-Blind Study", stated in the discussion, "The fact that negative air ionization prevents thromboembolism cannot be denied."In 1966 at a hospital in Jerusalem, doctors performed a series of tests on infants with similar respiratory problems. They divided the infants into two groups, in one group (the control group) no negative ion generator was used, and in another group a negative ion generator was used. The researchers reported that the negative ions, without any other treatment (no drugs), seemed to cure attacks of asthma and bronchitis quicker than drugs, antibiotics included. They also noted that no adverse side effects were found that are normally associated when treating children with drugs.

By improving overall health and well being, the positive effect the present art has on the population and work force cannot be denied. The use of the present device aids in treatment of SAD, asthma, etc. Consequently, it will save users (patients) millions in medical bills, And because the present invention will help prevent employees from calling in due to mental/health-related issue, companies will save millions of working hours. As a result, this invention will have a positive effect on the economy to the tune of millions of dollars.

There is no prior art that produces the unexpected results and the answers to a solution that has never been recognized. Moreover, the prior art teaches away from the present art in that it goes in a completely different direction. That is to say that the negative ion generators of the past, which are machines that produce negative ions (not a liquid solution of negative ions), were not designed for direct application to the skin or to be consumed as drink, etc., but were strictly designed for the production of negative ions. The present device, when placed in a humidifier, produces 2.5 times the concentration of negative ions than a commercially available ion generator machine.

A thorough search of patents, publications, and research revealed no relative art (i.e., prior art) showing any direct correlation to this novel invention. The search included the USPTO (United States Patent Office) data base with no patents issued for a device that is a liquid-stable solution of negative ions, which can be used for non-pharmacological treatment of multiple health and behavior issues.

SUMMARY OF INVENTION

The present invention is a method designed to advance the treatment of health and behavioral issues. This method relates to a liquid-stable solution of negative ions (to be referred to as "ions"). As previously discussed, negative ions have been demonstrated in numerous research papers and publications as having the ability to provide a non-pharmacologic therapy solution for many health and behavior issues.

The present art can be applied directly, sprayed, or misted on skin, and can also be inhaled. The ions solution can be placed in spray bottles, misters, humidifiers or other devices to disperse the solution into the air. Additionally, the ions solution can also be consumed as a drink for internal intake.

There is no prior art that demonstrates, teaches or even alludes to a liquid-stable solution of negative ions that can be used for non-pharmacologic treatment for depression, behavioral disorders (i.e. seasonal affective disorder (SAD)), and relief of headaches, earaches, stuffy/snotty noses from hay-fever allergies or colds, relief of asthma, bronchial asthma, bronchitis, thromboembolism, pain and peeling from sunburn or other burns, relief of itching from psoriasis, bug bites, or other skin irritations, as well as, improving memory, vitamin metabolism, sleeping patterns and behavior.

The present art allows for the use of a stable solution of negative ions, never before discovered, to aid in the treatment and prevention of disease. This art can be used without the use of electricity or other machines. The ions solution can be placed in spray bottles, inhalers, and misters or applied directly in the form of a bath or shower. The present art allows the user the ability to affect treatment without the need for machines or power remotely. Because no additional device is required to affect treatment, it will save the patient (user) consider amounts of money. In remote, third world countries, the solution could be used where power and machines are not available. However, this is not to say that the present art cannot use machines to affect treatment. The use of humidifiers and other devices that allow the dispersal of the ions solution into the air or onto a patients skin via a motorized inhaler, powered sprayer, or other such devices, are a distinct ability of the present device to affect treatment.

Correspondingly, another advantage of the present art is to provide a drinkable, stable solution to affect the ingestion of negative ions, a one step process which is not currently known in the art.

In addition, the present art provides for a unique method of increasing the amount of negative ions into the air while increasing the moisture (humidity) of a room, making it easier to breath in the aerosols of negative ions.

It has been found that the foregoing objects of the present art are accomplished in accordance with this invention by providing a stable solution of negative ions that can be immediately provided to the patient in a variety of methods.

The present invention provides a non-pharmacological method of treatment for health and behavioral problems in a human subject using a negative ion solution, with the method being characterized by the following steps: a) Exposing the subject to negative ions by contacting the subject with the negative ion solution in the form of spray, mist, or liquid; b) During exposure the negative ion solution comes into contact with the skin, lungs, mouth or other parts of the body to affect said treatment; and c) Said treatment occurs without the use of a negative ion generator.

Other aspects and advantages of the present invention appear more clearly from reading the following detailed description of the preferred embodiment of the invention, given by way of example and made with reference to the accompanying tables, such as, the determination of exactly how the device works. A thorough search of the literature reveals no relative art that resembles this technology; therefore, this invention is clearly novel in creation and is not obvious to anyone skilled in the art. In fact the prior art devices teaches away from the present art, in that the prior art requires a negative ion generator. With the present invention, there is no such generator requirement and, consequently, does not require manipulation or the essential need for electricity. Further, the prior art teaches away from the present device, in that, the prior art requires a generator that obviously requires electricity to affect treatment. There are certain aspects of the present art that can be found in the prior art (e.g. the use of negative ions), but no prior art has advanced the art of non-pharmacological treatment for health and behavioral problems and diseases. This invention solves an unrecognized problem that has never before been recognized. Specifically, this invention allows the user unexpected results through the use of a device that is simple, efficient, and cost effective and only utilizes a spray bottle, inhaler or other simple device to affect treatment, etc., for a much more effective, economical and practical method of treatment for depression, behavioral disorders (seasonal affective disorder (SAD)), headaches, earaches, stuff noses from hay-fever allergies or colds, asthma, bronchial asthma, and bronchitis, thromboembolism, pain and peeling from sunburn or other burns, itching from psoriasis, bug bites, or other skin irritations, as well as, improving memory, vitamin metabolism, sleeping patterns and behavior.

Therefore, with the present invention, it is very important that the ability to affect treatment without the use of a negative ion generator, electricity, or other machine virtually eliminates a problem or inability of the prior art.

DETAILED DESCRIPTION

The present invention will now be described more fully with reference to the accompanying tables, in which the preferred embodiments of the present art invention efficacy are shown. It is understood from the embodiments that a person skilled in the art may make variations and modifications without departing from the spirit and scope of the invention, such as, changing the formula's various component amounts, concentrations, or using similar but functional compounds. All accomplished while remaining within the scope and spirit of the invention.

The present invention is a method designed to advance the art of treatment for health and behavioral issues. This method relates to a liquid stable solution of negative ions (to be referred to as "ions"). Negative ions have been demonstrated in numerous research papers and publications to have the ability to provide a non-pharmacologic therapy solution for many health and behavior issues. The present art can be applied directly, sprayed, or misted on skin, and can also be inhaled. The ions solution can be placed in spray bottles, misters, humidifiers or other devices to disperse the solution into the air. The ions solution can also be consumed as a drink for internal intake.

The present invention is a liquid-stable solution of negative ions that can be used for non-pharmacologic treatment for depression, behavioral disorders (i.e. seasonal affective disorder (SAD)), relief of headaches, earaches, stuffy/snotty noses from hay-fever allergies or colds, relief of asthma, bronchial asthma, bronchitis, thromboembolism, pain and peeling from sunburn or other burns, relief of itching from psoriasis, bug bites, or other skin irritations, as well as, improving memory, vitamin metabolism, sleeping patterns and behavior. All of which are accomplished without the use of a negative ion generator.

The present art allows the use of a stable solution of negative ions never before discovered to aid in the treatment and prevention of disease. This art can be used without the use of electricity or machines to affect its ability to treat. The ions solution can be placed in spray bottles, inhalers, and misters or applied directly in the form of a bath or shower. The present art allows the user the ability to affect treatment without the need for machines or power remotely.

TABLE 1

Method Comparison (Measurements (ions/cm))

| Readings[1] | Neg Ion Generator[2] | Neg Ion Generator[3] | Humidifier[4] |
|---|---|---|---|
| 1 | −1300 | −1000 | −3000 |
| 2 | −1200 | −700 | −2800 |
| 3 | −1000 | −1200 | −3500 |
| Mean | −1167 | −967 | −3100 |

[1]The readings were taken using an "Air Ion Counter" from Alpha Lab, Inc.
[2]Negative Ion Generator from Comtech Research Model IG-133.
[3]Negative Ion Generator Model K-3000.
[4]Sunbeam"s 2 Gallon Cool Mist Humidifier containing the negative ion solution.

The study was conducted in an 18"×20" room over a three-day period. Conclusion of data from Table 1: the data clearly shows that the negative ion solution of the present invention produced more negative ions than two of the prior arts negative ion generators by a factor of 2.5 times without the use of a negative ion generator.

It is has been well published that negative ions affect serotonin levels in humans. It is also known that serotonin has been associated with and plays an important role in sleeping. In addition, negative ions have been demonstrated extensively to have positive affects on individuals suffering from depression and other behavioral disorders.

TABLE 2

Sleep Affects from Negative Ions Exposure

| Subject(s) Exposure[1] | No Humidifier | Humidifier[2] |
|---|---|---|
| 1 | No Noticeable affect | Sleep soundly without wakening |
| 2 | No Noticeable affect | Sleep soundly without wakening |
| 3 | No Noticeable affect | Sleep soundly (woke only once) |

[1]The different subject(s) were exposed to nightly sleep periods (typically 8 hours) with and without a humidifier.
[2]Sunbeam"s 2 Gallon Cool Mist Humidifier containing the negative ion solution.

Conclusion of data from Table 2: the data clearly shows that the humidifier containing the negative ion solution of the present invention produced a positive affect for sound sleep versus no humidifier with negative ion solution present. Although data not presented in this study was done in blind fashion with some subjects having no negative ion solution in there generators, in those subjects without the negative ion solution in their humidifiers (only water), there was no noticeable difference in their sleep pattern.

TABLE 3

Affect on Severe Colds, Stuffiness, and Earaches from Negative Ions Exposure

| Subject(s) Exposure[1] | No Humidifier | Humidifier(s)[2] |
|---|---|---|
| 1 | No Noticeable Affect | Cleared up cold and sleep soundly |
| 2 | No Noticeable Affect | Cleared/Stopped earache |
| 3 | No Noticeable Affect | Cleared Stuffy nose and tiredness |

[1]The different subject(s) ages from 14 to 73 were exposed to nightly sleep periods(typically 8 hours) with and without a humidifier.
[2]Humidifier(s) containing the negative ion solution.

Conclusion of data from Table 3: the data clearly shows that the humidifier containing the negative ion solution of the present invention produced a positive affect for clearing up colds, earaches, and stuffiness versus no humidifier with negative ion solution present.

TABLE 4

Affect on Asthma and Bronchitis from Negative Ions Exposure

| Subject(s) Exposure[1] | No Spray | Spray Bottle[2] |
|---|---|---|
| 1 | No noticeable affect | No coughing for two weeks after |
| 2 | No noticeable affect | Stopped attacks upon use |

TABLE 4-continued

Affect on Asthma and Bronchitis from Negative Ions Exposure

| Subject(s) Exposure[1] | No Spray | Spray Bottle[2] |
|---|---|---|
| 3 | No noticeable affect | No more episodes of asthma attacks |

[1]The different subject(s) were exposed to a spray bottle of negative ion solution spray directly into the mouth.
[2]Spray bottle containing the negative ion solution.

Conclusion of data from Table 4: the data clearly shows that the spray bottle containing the negative ion solution of the present invention produced a positive affect in regards to asthma, coughing and bronchitis-like syndromes. As supported by the multitude of studies, this data demonstrates the positive affect that negative ions can have on asthma and bronchitis. It may be noted that the subject(s) of the study stated that there was no need for an inhaler or other treatments for asthma while this study was being conducted.

TABLE 5

Affect on Sunburn, itching and other Burns from Negative Ions Exposure

| Subject(s) Exposure[1] | Spray Bottle[2] | Spray Bottle[3] |
|---|---|---|
| 1 | No Noticeable affect | Immediate Relief/No peeling |
| 2 | No Noticeable affect | No peeling |
| 3 | No Noticeable affect | Immediate Relief/No blister |
| 4 | No Noticeable affect | Immediate Relief/No blister |
| 5 | No Noticeable affect | Immediate Relief/No peeling |
| 6 | Continued Itching | Immediate Relief/No itching |
| 7 | Continued Itching | Immediate Relief/No itching |

[1]The different subject(s) were exposed to a spray bottle of negative ion solution spray directly onto the skin or area of exposure to sun, poison ivy, or stovetop.
[2]Spray bottle containing water.
[3]Spray bottle containing negative ion solution.

Conclusion of data from Table 5: the data clearly shows that the spray bottle containing the negative ion solution of the present invention produced a positive affect in regards to relieving suffering from sunburn/peeling, oven burns/blisters, and itching from poison ivy.

TABLE 6

Blind study designed to determine if any beneficial affect is received as a result of being exposed to the negative ion solution Exposure: Both arms of each subject were exposed to direct sunlight for a period of not less than 1 hour resulting in equal redness on both arms of each subject. This time of exposure varied depending upon skin type.

| Subjects | | H2O Exposure | Neg Ion Exposure | Initial Sensation | Relief of Pain After Spray |
|---|---|---|---|---|---|
| 1 | Left Arm | no | yes | cooling | yes |
|   | Right Arm | no | yes | cooling | yes |
| 2 | Left Arm | yes | no | cooling | no |
|   | Right Arm | yes | no | cooling | no |
| 3 | Left Arm | yes | no | cooling | no |
|   | Right Arm | no | yes | cooling | yes |
| 4 | Left Arm | no | yes | cooling | yes |
|   | Right Arm | yes | no | cooling | no |
| 5 | Left Arm | no | yes | cooling | yes |
|   | Right Arm | yes | no | cooling | no |
| 6 | Left Arm | no | yes | cooling | yes |
|   | Right Arm | yes | no | cooling | no |
| 7 | Left Arm | no | yes | cooling | yes |
|   | Right Arm | no | yes | cooling | yes |

Conclusion of data from Table 6: in the initial study, the negative ion solution appears to have a marked effect on relief of sunburn pain.

As illustrated in the data from the tables, the present art provides for a unique method of increasing the amount of negative ions into the air while increasing the moisture (humidity) of a room, making it easier to breath in the aerosols of negative ions.

It has been found that the foregoing objects of the present art are accomplished in accordance with this invention by providing a stable solution of negative ions that can be immediately provided to the patient in a variety of methods.

The present invention provides a non-pharmacological method of treatment for health and behavioral problems in a human subject using a negative ion solution, with the method being characterized by the following steps: a) Exposing the subject to negative ions by contacting the subject with the negative ion solution in the form of spray, mist, or liquid; b) During exposure the negative ion solution comes into contact with the subjects skin, lungs, mouth or other parts of the subjects body to affect said treatment; and c) Said treatment occurs without the use of a negative ion generator.

It should be noted that the discovery of the present invention was surprising and led to unexpected results in that it produced a stable solution of negative ions.

The following examples are provided to further illustrate the inventive aspects of the present discovery and to further describe preferred embodiments. As such, they are intended as being merely illustrative and are not to be construed as limiting the scope of the claims appended hereto.

EXAMPLE 1

The following procedure is a method for manufacturing a liquid stable solution of negative ions that can be placed in a humidifier, spray bottle, mister, inhaler, or consumed as a drink, used to shower with, or applied to the skin or body in some other manner or fashion while still remaining within the spirit and scope of the invention.

The liquid stable solution of negative ions is successively manufactured as follows: 1. Obtain 1 liter of distilled or deionized water.

2. Add 0.05 g polyphosphate (negative ion active ingredient) to 1 liter of water.

3. Mix until dissolved.

Once the above solution is completely dissolved in liquid, it is then store in a clean, dry container and tested for negative ion content by measuring the Zeta Potential (mV), which should be greater than −10.0 mV (e.g. the higher the mV reading the higher the negative ion concentration, that is to say that −50.0 mV is a higher negative ion concentration than −10.0 mV). The above solution is then placed in a spray bottle, humidifier, or other device so that the subject can be exposed to a negative ion solution, with the method being characterized by the following steps: a) Exposing the subject to negative ions by contacting the subject with the negative ion solution in the form of spray, mist, or liquid; b) During exposure the negative ion solution comes into contact with the subjects skin, lungs, mouth or other parts of the subjects body to affect said treatment; and c) Said treatment occurs without the use of a negative ion generator.

It should be noted that the discovery of the present invention was surprising and led to unexpected results in that it produced a stable solution of negative ions.

The negative ion, active ingredient polyphosphate, used in example 1, may be substituted with one or more selected from the group consisting of sodium tripolyphosphate, pentasodium triphosphate, carrageenan, irish moss extracts, sea weed extracts, red seaweed extracts, beta-1,3-Dgalactose and alpha-1,4-3,6-anhydro-D-galactose polysaccharides, polysaccharides, polyanions, phycocolloids, sodium carrageenan, potassium carrageenan, calcium carrageenan, or a salt form of carrageenan, extracts of kelp, extracts of alaria, and extracts of laver-nori.

Note that the above could additionally be substituted with any other chemical or compound with the ability to produce a stable, high negative ion concentration in a liquid and can be used as defined by the present art while still falling within the spirit and scope of the present invention.

EXAMPLE 2

The following procedure is a method for manufacturing a liquid stable solution of negative ions that can be placed in an humidifier, a spray bottle, mister, inhaler, or consumed as a drink, used to shower with, or applied to the skin or body in some other manner or fashion and still remain within the spirit and scope of the invention.

The liquid stable solution of negative ions is successively manufactured as follows: 1. Obtain 1 liter of distilled or deionized water.

2. Add 0.05 g carrageenan (negative ion active ingredient) to 1 liter of water.

3. Mix until dissolved.

Once the above solution is completely dissolved in liquid, it is then store in a clean, dry container and tested for negative ion content by measuring the Zeta Potential (mV), which should be greater than −10.0 mV (e.g. the higher the mV reading the higher the negative ion concentration, that is to say that −50.0 mV is a higher negative ion concentration than −10.0 mV). The above solution is then placed in a spray bottle, humidifier, or other device so that the subject can be exposed to a negative ion solution, with the method being characterized by the following steps: a) Exposing the subject to negative ions by contacting the subject with the negative ion solution in the form of spray, mist, or liquid; b) During exposure the negative ion solution comes into contact with the subjects skin, lungs, mouth or other parts of the subjects body to affect said treatment; and c) Said treatment occurs without the use of a negative ion generator.

It should be noted that the discovery of the present invention was surprising and led to unexpected results in that it produced a stable solution of negative ions. The negative ion, active ingredient carrageenan, used in example 2, may be substituted with one or more selected from the group consisting of: polyphosphate, sodium tripolyphosphate, pentasodium triphosphate, irish moss extracts, sea weed extracts, red seaweed extracts, beta-1,3-Dgalactose and alpha-1,4-3,6-anhydro-D-galactose polysaccharides, polysaccharides, polyanions, phycocolloids, sodium carrageenan, potassium carrageenan, calcium carrageenan, or a salt form of carrageenan, extracts of kelp, extracts of alaria, and extracts of laver-nori.

Note the above could additionally be substituted with any other chemical or compound with the ability to produce a stable high negative ion concentration in a liquid and can be used as defined by the present art while still falling within the spirit and scope of the present invention. The following is a brief explanation of the novel, present art. It is a non-pharmacological method of treatment for health and behavioral problems in a human subject using a negative ion solution comprising the steps of producing a negative ion solution with a zeta ion potential of at least −10 mV or greater by successively dissolving a negative ion active ingredient completely in water, and; exposing the subject to negative ions by contacting the subject with the negative ion solution in the form of spray, mist, humidifier, inhaler, liquid drink or shower, without the use of a negative ion generator. As taught, the negative ion active ingredient can be selected from the group consisting of: polyphosphate, sodium tripolyphosphate, pentasodium triphosphate, carrageenan, irish moss extracts, sea weed extracts, red seaweed extracts, beta-1,3-D-galactose and alpha-1,4-3,6-anhydro-D-galactose polysaccharides, polysaccharides, polyanions, phycocolloids, sodium carrageenan, potassium carrageenan, calcium carrageenan, or a salt form of carrageenan, extracts of kelp, extracts of alaria, or extracts laver-nori. It is also understood that the water used in the prior examples can be substituted with other suitable solvents selected from the group consisting of: alcohols, buffers, or organic solvents. As made apparent, when using a spray, mist, inhaler, liquid drink or shower, the present art does not require electricity.

This invention is going to save the general public, government and private enterprise millions of dollars in time and labor. It is a well-known fact that millions of dollars are spent daily on health care and medicine for symptoms of flu, cold, depression, etc The use of the present invention will make for a healthier world.

Further, the invention has been described in detail with particular reference to a preferred embodiment and the operation thereof, and it is understood that variations, modifications, and substitution of equivalent means can be effected and still remain within the spirit and scope of the invention. All such modifications and variations are to be included within the scope of the invention as defined in the appended claims.

The invention claimed is:

1. A method of improving the health of a human subject, comprising the steps of:

providing a solution with a negative zeta potential of at least −10 mV by dissolving carrageenan in a solvent; and contacting the subject with the solution by transdermal application of the solution, inhalation of the solution, or imbibition of the solution.

2. The method of claim 1 wherein the solvent is selected from the group consisting of deionized water, distilled water, alcohols, buffers, and organic solvents.

3. The method according to claim 1, wherein said solution is provided in a form selected from the group consisting of a mist, a liquid and a shower.

4. The method according to claim 1, wherein said solution is dispersed by an apparatus selected from the group consisting of a humidifier and an inhaler.

5. A method of improving the health of a human subject, comprising the steps of:

providing a solution with a negative zeta potential of at least −10 mV by dissolving a negative ion active ingredient in a solvent, said negative ion active ingredient is selected from the group consisting of: carrageenan, Irishmoss extracts, sea weed extracts, red seaweed extracts, polyanions, sodium carrageenan, potassium carrageenan, calcium carrageenan, and a salt form of carrageenan, extracts of kelp, extracts of alaria, and extracts of laver-nori; and contacting the subject with the solution containing the dissolved negative ion active ingredient, wherein the step of contacting the subject is selected from the group consisting transdermal application of the solution, inhalation of the solution, and imbibition of the solution.

6. The method of claim 5 wherein the solvent is selected from the group consisting of deionized water, distilled water, alcohols, buffers, and organic solvents.

7. The method according to claim 5, wherein said solution is in the form of a mist.

8. The method according to claim 5, wherein said solution is dispersed by a humidifier.

9. The method according to claim 5, wherein said solution is dispersed by an inhaler.

10. The method according to claim 5, wherein said solution is in the form of a liquid.

11. The method according to claim 5, wherein said solution is in the form of a shower.

\* \* \* \* \*